(12) United States Patent
Hadala et al.

(10) Patent No.: US 8,367,123 B2
(45) Date of Patent: Feb. 5, 2013

(54) SUPPLEMENT FORMULA TO PREVENT AND DETER MUSCLE TRAUMA AND METHOD OF USING SAME

(75) Inventors: Anthony J. Hadala, Sagamore Hills, OH (US); Lewis E. Bennett, Hudson, OH (US)

(73) Assignee: Muscle Sentry LLC, Northfield, OH (US)

( * ) Notice: Subject to any disclaimer, the term of this patent is extended or adjusted under 35 U.S.C. 154(b) by 289 days.

(21) Appl. No.: 12/503,235

(22) Filed: Jul. 15, 2009

(65) Prior Publication Data

US 2010/0015118 A1 Jan. 21, 2010

Related U.S. Application Data

(60) Provisional application No. 61/135,052, filed on Jul. 16, 2008, provisional application No. 61/176,192, filed on May 7, 2009.

(51) Int. Cl.
*A61K 36/00* (2006.01)
(52) U.S. Cl. ...................................................... 424/725
(58) Field of Classification Search .................. 424/725, 424/775
See application file for complete search history.

(56) References Cited

U.S. PATENT DOCUMENTS

2008/0119426 A1* 5/2008 Dale ............................... 514/44

OTHER PUBLICATIONS

Felter M.D., et al., King's American Dispensatory, Nineteenth Ed., 1905, pp. 543, 551 and 552.*

* cited by examiner

*Primary Examiner* — Patricia Leith
(74) *Attorney, Agent, or Firm* — Rankin, Hill & Clark LLP

(57) ABSTRACT

A body supplement and method for improving blood flow, muscle chemistry and/or the oxygenation of muscles, said supplement including cinchona bark or quinine in the range of approximately 0.0010 grams and 4.0 grams per dosage.

19 Claims, No Drawings

SUPPLEMENT FORMULA TO PREVENT AND DETER MUSCLE TRAUMA AND METHOD OF USING SAME

This application claims priority in Provisional Patent Application Ser. No. 61/135,052 filed on Jul. 16, 2008 and Provisional Patent Application Ser. No. 61/176,192 filed on May 7, 2009 which are both incorporated by reference herein.

The invention of this application relates to supplements and, more particularly, to supplements that help improve the physical characteristics of the muscles.

INCORPORATION BY REFERENCE

U.S. Patent Publication No. 2006/0148841 discloses a medicinal composition and is incorporated by reference herein for showing the same. U.S. Patent Publication No. 2001/0008641 discloses a nutritionally active composition for bodybuilding and is incorporated by reference herein for showing same.

BACKGROUND OF THE INVENTION

The invention of this application relates to supplements and, more particularly, to supplements that help improve the physical characteristics of the muscles. It has been found that these supplements work well when used for human muscles and, therefore, it will be described in connection with human applications. However, the invention of this application has broader applications and should not be limited to only human uses.

Thousands of athletes are sidelined by serious injuries to their muscles each day. Whether the injury is a minor pulled muscle or a serious torn hamstring, these injuries are troublesome to all athletes.

These injuries can happen when the muscles are not properly warmed up before hard physical exercise or exertion even in the well trained athlete. Often, many younger athletes believe they are impervious to injury and often do not fully warm their muscles before or during athletic practices. This can result in short term and long term injuries that can plague an athlete for the next game or for an entire season.

While it has been found that proper stretching and warming up of the muscles can prevent these injuries, that is not always the case and injuries often sideline the best of athletes.

SUMMARY OF THE INVENTION

The invention of this application relates to supplements and, more particularly, to supplements that can be used to prevent muscle trauma and/or to increase muscle performance.

In greater detail, the supplements of this application balance the muscle's chemistry to deter hyper-contraction of the muscle and/or to improve the performance of the muscle.

According to one aspect of the invention of this application, the supplement includes an effective amount of cinchona bark or quinine.

According to another aspect of the invention of this application, the supplement further includes other ingredients that can be used to improve the chemistry of the muscles. In one embodiment, these other ingredients are calcium, magnesium and manganese.

According to a further aspect of the invention of this application, the supplement can include an effective amount of a quinine or cinchona bark in a raw state before refinement, a processed state, and/or any derivatives thereof.

According to yet a further aspect of the invention of this application, a method of administering the supplement is provided wherein the supplement is administered before, during exertion or exercise and/or after the physical activity.

The foregoing, and more, will in part be obvious and in part be pointed out more fully hereinafter in conjunction with a written description of preferred embodiments of the present invention set forth below.

DESCRIPTION OF PREFERRED EMBODIMENTS

In one embodiment, the present invention relates to a supplement and a method of using and/or administering the supplement to improve the performance of ones muscles and improve the effectiveness of a workout or physical activity. This can be achieved by using cinchona bark or quinine to balance the chemistry in the muscles of the body before or during exercise or exertion.

Further, it has been found that cinchona bark or quinine can be a conductor to improve the performance of other supplements to improve muscle chemistry during physical activities. This has been found to work especially well to prevent muscle damage that is often caused when athletes do not properly warm up and/or stretch. However, it has also been found that the use of the supplement according to one or more aspects of the present invention can have a beneficial effect even when athletes properly warm up and stretch by increasing the effectiveness of these activities and/or reducing the amount of time needed for both.

As is known in athletics, practice is important and physical activity is important to improve ones endurance, muscle tone and abilities; however, the time needed to prepare for such physical activity is often considered to be wasteful since this preparation time does not add to ones physical abilities. As a result, athletes often spend too little time stretching and warming up to help maximize the time that can be used for strength training and practicing for a sport. Over the years, it has been found that this is foolish, but when time is at a premium, athletes often use only a minimal time for proper warm up.

This is especially true for the people that use physical activity for only weight loss and muscle tone.

By using the combination of herbs and minerals of the supplement of this application, the muscle chemistry can be balanced and hyper-contraction of the muscle can be minimized. It has been found that the balance of the minerals in your muscles is important to muscle health. When this balance is off, muscle problems often arise such as muscle pulls, muscle spasms, muscle strains and other muscle problems. However, when muscle chemistry is properly balanced, these conditions are minimized or eliminated.

The muscle can be compared to a guitar string wherein it is stretched tight and the muscle moves calcium from one end to the other during physical activity. By using a mixture of the supplement of this application, this tight string can be relaxed at least some to prevent it from overstretching which can result in an injury. This relaxing of the muscle is from balancing the chemistry of the muscle according to the invention of this application. At least in part, this balance of chemistry is a balance of the mineral content of the muscle which has been found to greatly reduce the likelihood of muscle damage or strain during physical activity.

In one embodiment, the supplement includes cinchona bark in any one of a number of forms. This can include, but is not limited to, red, yellow and brown cinchona bark hereinafter collectively referred to as cinchona bark. The cinchona bark can be used in combination with other supplements and can act as a conductor to improve the performance of these other supplements. Further, the cinchona bark itself has performance improving properties for the muscles of the body along with other benefits that will be discussed in greater detail below.

In one set of embodiments, the cinchona bark ranges, per dosage, between 0.0010 grams and 4.0 grams for the supplement. In yet other embodiments, the cinchona bark is in the range of 0.0025 gram to 2.0 grams. In other embodiments, the range is between approximately 0.10 grams and 0.50 grams of cinchona bark. In yet further embodiments, approximately 0.30 grams of cinchona bark is used per dosage.

Further, in yet another embodiment, it has been found that this supplement can be administered more than once in a given day with one of the embodiments including two dosages of supplement having approximately 0.20 to 0.40 grams of cinchona bark with a total daily dosage of below around 4 grams of cinchona bark.

In yet other embodiments of this application, the cinchona bark is replaced with quinine and/or other processed derivatives of the cinchona bark or quinine.

In yet other embodiments, the supplement of this application is administered before a physical activity such as, but not limited to, an exercising activity. In yet further embodiments, it is also administered during the physical activity. This can include taking a first dosage of the supplement up to approximately 1.5 hours hour before the activity and then a second dosage part way through the activity. Depending on the method of administering, this time can vary and in some embodiments it is a dosage approximately 1.0 hours or 0.5 hours before the activity. It has been found that the second dosage works particularly well if taken half way through the activity, but this not required. In all embodiments of this application, dosage can mean a single unit taken by the user or multiple units taken by the user which are smaller in quantity and which are meant to maintain a more even and consistent muscle chemistry during a particular stage of activity. Thus, dosage as used in this application should not be limited to a single unit taken.

By using the supplement according to the invention of this application before the physical activity, the user's muscles are essentially pre-warmed so that they are less likely to be strained during warm-up or with inadequate warm-up. In addition, the chemistry of the muscles is improved wherein the physical activity is more effective and blood flow is increased throughout the body.

In addition, supplements according to the invention of this application can improve cardio function, help regulate the user's heartbeat and function, prevents and/or relaxes muscle trauma or convulsions. Yet even further, the supplement can improve digestive and thyroid function.

By using the supplement according to the invention of this application during physical activity, such as mid way through the activity, these benefits can effectively continue throughout the workout.

In yet other embodiments, the supplement can further include one or more of the following:

Quinine or quinine alkaloids. These can be used to prevent and/or relax muscle trauma or convulsion. In one embodiment, the dosage includes between 200 mg and 350 mg of quinine or quinine Alkaloids. In another embodiment, the supplement includes approximately 325 mg of quinine or quinine Alkaloids.

Calcium which can be a muscle contraction facilitator. In one embodiment, the dosage includes between 400 mg and 1200 mg of Calcium. In another embodiment, the supplement includes less than 1,000 mg of Calcium.

Manganese which can facilitate Calcium absorption. In one embodiment, the dosage includes between 5 mg and 25 mg of Manganese. In another embodiment, the supplement includes less than 20 mg of Manganese.

Vitamin E or D-Alpha Tocopheryl Acetate which can be used as an Antioxidant. In one embodiment, the dosage includes between 15 IU and 60 IU of Vitamin E or D-Alpha Tocopheryl. In another embodiment, the supplement includes less than 30 IU of Vitamin E or D-Alpha Tocopheryl.

Wheat Germ Oil which can be used as an Amino Acid. In one embodiment, the dosage includes between 100 mg and 275 mg of Wheat Germ Oil—Amino Acid. In another embodiment, the supplement includes less than 250 mg of Wheat Germ Oil.

Potassium and/or Potassium Chloride which can be used to facilitate calcium absorption. In one embodiment, the dosage includes between 400 mg and 1600 mg of Potassium and/or Potassium Chloride. In another embodiment, the supplement includes less than 1,500 mg of Potassium and/or Potassium Chloride.

Niacin which can be used as a vasodilator. In one embodiment, the dosage includes between 100 mg and 220 mg of Niacin. In another embodiment, the supplement includes less than 200 mg of Niacin.

Vitamin B6 which can be used as a nervous system modulator. In one embodiment, the dosage includes between 10 mg and 60 mg of Vitamin B6. In another embodiment, the supplement includes less than 50 mg of Vitamin B6.

Vitamin B12 which also can be used as a nervous system modulator. In one embodiment, the dosage includes between 40 mcg and 80 mcg of Vitamin B12. In another embodiment, the supplement includes less than 75 mcg of Vitamin B12.

Fish Oil which can be used as an antioxidant. In one embodiment, the dosage includes between 400 mg and 1200 mg of Fish Oil. In another embodiment, the supplement includes less than 1,000 mg of Fish Oil.

Flaxseed Oil which also can be used as an antioxidant. In one embodiment, the dosage includes between 400 mg and 1200 mg of Flaxseed Oil. In another embodiment, the supplement includes less than 1,000 mg of Flaxseed Oil.

Borage Oil which also can be used as an antioxidant. In one embodiment, the dosage includes between 400 mg and 1200 mg of Borage Oil. In another embodiment, the supplement includes less than 1,000 mg of Borage Oil.

Omega 3 Fatty Acids which can be used as an antioxidant. In one embodiment, the dosage includes between 400 mg and 1200 mg of Omega 3 Fatty Acids. In another embodiment, the supplement includes less than 1,000 mg of Omega 3 Fatty Acids.

Magnesium which can be used to improve waste product elimination in muscle tissue. In one embodiment, the dosage includes between 300 mg and 600 mg of Magnesium. In another embodiment, the supplement includes less than 500 mg of Magnesium.

In yet other embodiments of the invention of this application, the supplement can include the following secondary ingredients which can also improve the performance of the supplement of this application. These secondary ingredients can include one or more of the following ingredients that can be used in combination with one or more of the ingredients referenced above. These ingredients have their own benefit and can be also used to meet daily allowance for certain supplements. These include the following:

Vitamin C which can also be used as an antioxidant. In one embodiment, the dosage includes between 500 mg and 1,600 mg of Vitamin C. In another embodiment, the supplement includes less than 1,500 mg of Vitamin C.

Thiamin which can be used as a nervous system modulator. In one embodiment, the dosage includes between 30 mg and 120 mg of Thiamin. In another embodiment, the supplement includes less than 100 mg of Thiamin.

Riboflavin which can also be used as a nervous system modulator. In one embodiment, the dosage includes between 30 mg and 120 mg of Riboflavin. In another embodiment, the supplement includes less than 100 mg of Riboflavin.

Pantothenic Acid which can be used as an amino acid. In one embodiment, the dosage includes between 3 mg and 12 mg of Pantothenic Acid. In another embodiment, the supplement includes less than 10 mg of Pantothenic Acid.

Zinc which can be used as an antioxidant and/or a detoxifier of cellular byproducts. In one embodiment, the dosage includes between 80 mg and 175 mg of Zinc. In another embodiment, the supplement includes less than 150 mg of Zinc.

Chromium which can be used to facilitate cellular metabolism. In one embodiment, the dosage includes between 60 mcg and 150 mcg of Chromium. In another embodiment, the supplement includes less than 120 mcg of Chromium.

Sodium which can be used as a functional conductor of electrical stimulus. In one embodiment, the dosage includes between 100 mg and 250 mg of Sodium. In another embodiment, the supplement includes less than 200 mg of Sodium.

Alpha-Linolenic Acid (ALA) which can be used as a source of amino acid. In one embodiment, the dosage includes between 300 mg and 600 mg of ALA. In another embodiment, the supplement includes less than 500 mg of ALA.

Eicosapentagnoic Acid (EPA) which can also be used as a source of amino acid. In one embodiment, the dosage includes between 150 mg and 350 mg of EPA. In another embodiment, the supplement includes less than 500 mg of EPA.

Docosahesaenoic Acid (DHA) which can also be used as a source of amino acid. In one embodiment, the dosage includes between 100 mg and 250 mg of DHA. In another embodiment, the supplement includes less than 200 mg of DHA.

Gamma Linolenic Acid (GLA) which can also be used as a source of amino acid. In one embodiment, the dosage includes between 100 mg and 250 mg of GLA. In another embodiment, the supplement includes less than 200 mg of GLA.

Caffeine which can be used as a vasodilator. In one embodiment, the dosage includes between 30 mg and 600 mg of Caffeine. In another embodiment, the supplement includes less than 500 mg of Caffeine.

As is known in the art, amino acids are essential building blocks for muscles and which have been found to complement other ingredients of the supplement of this application. Antioxidants are essential to cellular metabolism. As is also known in the art, dosages may vary with size of the athlete and the nature of the physical activity. However, it has been found that a single formulation of these ingredients can be used for a wide range of athletes or people who do extreme physical work.

In one embodiment, the supplement of this application includes between approximately 200 and 400 mg of cinchona bark, between 400 mg and 1200 mg of calcium, between 5 mg and 25 mg of manganese and between 300 mg and 600 mg of magnesium. This combination has been found to work particularly well to promote the proper muscle chemistry. With respect to the cinchona bark, it has been found to not only have its own benefits on muscle health, but to also act as a conductor to improve the performance of the other ingredients in the supplement.

In yet other embodiments, vitamin E, wheat germ oil, potassium, niacin, vitamin B6 and/or caffeine are added to the cinchona bark, calcium, manganese and magnesium. This combination further enhances the performance of the supplement. In even yet another embodiment, it has been found that the supplement works particularly well when it includes cinchona bark, calcium, manganese, magnesium, vitamin E, wheat germ oil, potassium, niacin, vitamin B6 and caffeine.

In yet other embodiments, the supplement, including cinchona bark or quinine, is used to pre-oxygenate the muscle to help in the warming up of the muscle or during the physical activity.

The supplement of this application can come in any form known in the industry including, but not limited to, a liquid form, powdered form, and/or a solid, pill form, capsule form, or even gas form. As a result, the delivery of the supplement can be in any way known in the art including, orally or intravenously or even by way of nasal delivery. Oral applications can be by any way known in the art including by way of a liquid. Sublingually, dissolving strips taken orally, liquid drink style forms, within beverages, as part of a food supplement such as an energy bar, within gum or candy. Another method of administering the supplement is in a patch form wherein the patch can be designed to last for the typical duration of a particular activity or even for set amounts of time. Further, other delivery forms known in the art could be used without detracting from the invention of this application.

In yet other embodiment, the supplement can have a wide range of other ingredients not specifically listed in this application. This can include ingredients that are non-essential to muscle chemistry, but have other purposes. This can include, but is not limited to, ingredients that make the product taste better or ingredients that help supply the body with sources of energy which are known in the industry to help in physical activity. For example, the supplement of this application can be used in combination which an energy bar and/or an energy drink wherein the energy bar or drink provide all or some of the calories and/or hydration that are needed to sustain physical activity.

The uses of this supplement are also broad wherein they can be sports related, exercise related or for other physical activities such as hiking, rock climbing, bike riding, skiing and the like.

When taken properly, the supplement of this application can prevent and/or deter muscle damage or trauma. Further, it can improve the effectiveness of the physical activity. This can include, but is not limited to, preventing or deterring muscle spasms or cramping. Further, the supplement of the invention of this application also improves cardiovascular function and improves muscle function.

It has also been found that the supplement of this application can be used to improve digestive function thus increasing metabolism and to increase the body's ability to repair injury and recovery time. It can also improve the body's ability to eliminate waste products, thus boosting immunity and defense. This, and other embodiments, can be enhanced with other products including, but not limited to, nutritional products such as whole or multi-grain ingredients.

In yet another embodiment, the supplement can be used to increase concentration skills and can be used to increases libido and anatomical function, male and female. This is accomplished by the supplements ability to increase blood flow throughout the body. This increased blood flow not only improves the function of the muscles, but also improves the function of other parts of the body which can benefit from improved circulation. This can also include improvements to thyroid function.

Not only has it been found that the supplement of this application can improve one's physical activity or prevent damage to the body, it has also been found to increase muscle recovery after exercise. This can be the regeneration of the breakdown of muscle tissue during normal exercise and also the healing of muscle damage during exercise.

In view of the improvements to circulation and body performance, the supplement of this application is also believed to have an affect on the cancerous cells and their growth. In this respect, and as is known, a strong body is better able to fight cancer and the growth of cancer cells. As a result, the supplement of this application may prevent or treat cancer.

The supplement of the invention of this application can be used to prevent or deter muscle damage or trauma as the muscle is warming up and/or during exercise. Since the muscle gets more oxygen or blood flow, there is a reduced chance of damage during warm up. Further, this improved flow improves muscle chemistry which can improve the effectiveness of physical activity. In addition, the invention can also reduce the heart rate during physical activity wherein it has been found that the heart rate can be reduced by between 2 percent and 15 percent. This reduction in the heart rate also improves the effectiveness of the physical activity by maintaining the body's system in a more ideal condition. In yet other embodiment, the supplement is configured to reduce the heart rate wherein it has been found that the heart rate can be reduced by between 2 percent and 8 percent by reducing the amount of cinchona bark.

Further, the supplement of this application can provide additional oxygen so that this oxygenation reduces the amount that the heart needs to work; making it more efficient to achieve the same amount of oxygen and/or blood in the system which at least in part produces the reduction of the heart rate.

In yet other embodiments, the supplement of this application can be used to have a thermogenic effect to stimulate the body's burning of fat. This effect increases the metabolism of the body's adipose tissue, generating heat.

The increase in blood flow and body performance can also improve the pores of the skin by increasing the blood flow through the skin which could help prevent acne or heal acne.

In yet another embodiment, more than one supplement can be used for a given activity. More particular, the supplement can come in different forms for different states of the activity. This can include a first supplement configured to get the body prepared for physical activity. This first supplement would have a higher dosage of cinchona bark and/or any other supplement. For example, this first supplement could have a dosage of between approximately 2.0 and 3.0 grams of cinchona bark which will quickly start the beneficial effects of the supplement. This could then be followed by a second dosage that would be in the range of approximately 1.0 and 2.0 grams of cinchona bark to maintain the body. This could then be followed by other dosages; however, as can be appreciated, the number of doses would affect the amount per dosage. The same is true for the other ingredients wherein the first dosage would be nearer to the high side of the ranges stated above and the second or following dosage would be approximately half the dosage to maintain the body's increased performance.

As can be appreciated, these dosages in stages could have a wide range of alteration without detracting from the invention of this application. This can include a third stage which is configured for muscle healing which would include more of the supplements that are tailored to muscle healing and regeneration.

Further, the invention of this application could also come in the form of a kit which includes these different states of dosages. Also, this kit could be configured for a specific type of physical activity. As can be appreciated, the physical activity of weight lifting can be different than that of long distance running wherein the weight lifting kit could be a stronger and shorter dosage while distance runners would use smaller dosages or even a patch version of the invention as opposed to a quick nasal dosage. These kits can be in the form of multiple dosages of an effective amount of the supplements according to at least one embodiment of this application in disposable packages having each dosage in a separate compartment within the package. These separate compartments can be separately sealed compartments wherein each dosage can be removed without disturbing the seal of other dosages. These dosages can be in any form which is known in the art and/or which is referenced in this application. This can include, but is not limited to, individual pills, individual packets of liquid or even individual packets of a powder. In yet other embodiments, these individual packets can be configured to be added to a liquid such that the dosage administered before, during or afterwards, become a plurality of dosages taken each time the user takes a drink. As can be appreciated, the supplement of the invention of this application could be the drink itself.

The kit according to another aspect of the present invention can include instructions printed thereon or printed within the kit. As can be appreciated, these kits could also be packaged as a plurality of kits sold at one time. An example is a weeks worth of kits or even a month worth of kits being packaged together. The user of the supplements of this application provided in kit form could then just remove one kit at a time which would represent use for a single workout regimen or any other physical activity. The user would then take each dosage at the designated time relative to the workout or physical activity.

This can include providing a kit having more than one dosage of the supplement of this application and the use of these supplements would include the steps of taking a first dosage from the kit having a first effective amount of the supplement a set time before the particular physical activity;

performing a physical activity;

Then, during this physical activity, taking a second dosage from the kit having a second effective amount of a supplement according to one or more embodiments of this application. This second dosage can be the same or similar to the first dosage or could be a different embodiment of this application. The second dosage can compliment the first dosage and/or can maintain the enhancing effect of the first dosage relating to the muscle chemistry during the particular physical workout. This can include improving blood flow and the oxygenation of muscles;

The kit could also include a third dosage for after the workout.

In yet other embodiments, one or more of the "dosages" could be replaced with multiple smaller dosages which can be used to maintain a more even flow of the supplement through the body and the kit can include these multiple dosages.

In yet other embodiments, these pluralities of first, second and/or third dosages, can include one or more ingredient that are incrementally increasing and/or decreasing. For example, the amounts of the ingredients that promote blood flow and the pre-oxygenation of the muscles can start high, such as a first dosage of between 0.20 and 0.40 grams of cinchona bark wherein the subsequent dosages of cinchona bark can taper off to less than 0.10 grams for the final dosage. Similarly, the ingredients configured to rebuild damaged tissue, such as calcium, manganese, and magnesium, can be administered in higher amounts in the later dosages.

While considerable emphasis has been placed on the preferred embodiments of the invention illustrated and described herein, it will be appreciated that other embodiments and/or equivalents thereof can be made and that many changes can be made in the preferred embodiments without departing from the principles of the invention. Accordingly, it is to be distinctly understood that the foregoing descriptive matter is to be interpreted merely as illustrative of the invention and not as a limitation.

It is claimed:

1. A method for preventing muscle trauma and increasing muscle performance in an athlete, wherein said method comprises:
   an athlete performing a strenuous physical activity, whereby
   before initiation of said strenuous physical activity, the athlete is administered a dosage comprising:
   about 100 to about 600 mg of cinchona bark.

2. The method of claim 1, wherein said dosage comprises about 100 to about 300 mg of cinchona bark.

3. The method of claim 1, wherein said dosage comprises about 300 mg to 600 mg of cinchona bark.

4. The method of claim 1, wherein said dosage comprises about 100 mg to 500 mg of cinchona bark.

5. The method of claim 1, wherein said dosage comprises about 600 mg of cinchona bark.

6. The method of claim 1, wherein said dosage comprises about 300 mg of cinchona bark.

7. The method of claim 1, wherein cinchona bark is in the form of a powder and wherein the dosage further comprises at least one selected from the group consisting of niacin, vitamin B6, calcium, magnesium, zinc, manganese and potassium.

8. The method of claim 1, wherein the cinchona bark is in liquid form.

9. The method of claim 8, wherein the dosage further comprises at least one selected from the group consisting of niacin, vitamin B6, calcium, magnesium, zinc, manganese and potassium.

10. The method of claim 1, wherein the dosage is administered approximately 1.5 hours before said strenuous physical activity.

11. The method of claim 1, wherein the dosage is administered approximately 0.5 hours before said strenuous physical activity.

12. The method of claim 1, wherein the dosage is administered approximately 1.0 hours before said strenuous physical activity.

13. The method of claim 1, further comprising providing to said athlete, a second dosage of cinchona bark during said strenuous physical activity.

14. The method of claim 13, wherein the amount of cinchona bark in said second dosage is less than the amount of cinchona bark in the dosage administered before said strenuous physical activity.

15. The method of claim 14, further comprising providing to said athlete, a third dosage of cinchona bark after administration of said second dosage of cinchona bark, wherein said third dosage is administered after said strenuous activity.

16. The method of claim 15, wherein the amount of cinchona bark in said third dosage is less than the amount of cinchona bark in the second dosage of cinchona bark.

17. The method of claim 13, wherein the amount of cinchona bark in said second dosage is greater than the amount of cinchona bark in the dosage administered before said strenuous physical activity.

18. The method of claim 17, further comprising providing to said athlete, a third dosage of cinchona bark after administration of said second dosage of cinchona bark, wherein said third dosage is administered after said strenuous activity.

19. The method of claim 18, wherein the amount of cinchona bark in said third dosage is greater than the amount of cinchona bark in the second dosage of cinchona bark.

* * * * *